United States Patent
Shintaku et al.

(10) Patent No.: US 6,333,430 B1
(45) Date of Patent: Dec. 25, 2001

(54) PROCESS FOR PREPARING TERT-ALKYL ESTER FROM CARBOXYLIC ACID

(75) Inventors: Tetsuya Shintaku; Kiyoshi Sugi; Tadashi Katsura; Nobushige Itaya, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/561,993

(22) Filed: May 2, 2000

(30) Foreign Application Priority Data

May 7, 1999 (JP) .................................. 11-127565

(51) Int. Cl.$^7$ .................................. C07C 67/04
(52) U.S. Cl. .................. 560/203; 560/204; 560/241; 560/247
(58) Field of Search .................. 560/203, 204, 560/226, 233, 241, 242, 247, 222

(56) References Cited

U.S. PATENT DOCUMENTS

| 2,217,735 | 10/1940 | Dreyfus . |
| 5,591,888 | 1/1997 | Seidel et al. . |

FOREIGN PATENT DOCUMENTS

| 4434444 A | 3/1996 | (DE) . |
| 1264824A | 10/1961 | (FR) . |

OTHER PUBLICATIONS

Organic Synthesis III, pp. 140–147 (1955).
Organic Synthesis IV, pp. 260–267 (1963).
Tetrahedron Letters, 38(42) pp. 7345–7348 (1997).

*Primary Examiner*—Sreeni Padmanabhan
*Assistant Examiner*—Sikarl A. Witherspoon
(74) *Attorney, Agent, or Firm*—Birch, Stewart, Kolasch & Birch, LLP

(57) ABSTRACT

A process for preparing a tert-alkyl carboxylic acid ester represented by the formula (III):

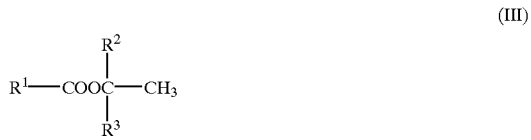

(III)

wherein $R^1$ is an organic group; and each of $R^2$ and $R^3$ is independently an alkyl group having 1 to 4 carbon atoms, comprising reacting a carboxylic acid represented by the formula (I):

$$R^1\text{---COOH} \qquad (I)$$

wherein $R^1$ is as defined above, with a vinylidene compound represented by the formula (II):

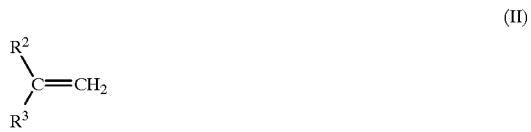

(II)

wherein $R^2$ and $R^3$ are as defined above, in the presence of a phosphorus halide. The tert-alkyl carboxylic acid ester can be used as intermediates for pharmaceuticals such as antibiotics.

4 Claims, No Drawings

PROCESS FOR PREPARING TERT-ALKYL ESTER FROM CARBOXYLIC ACID

BACKGROUND OF THE INVENTION

1. Field of the Invention

The present invention relates to a process for preparing a tert-alkyl carboxylic acid ester. More specifically, the present invention relates to a process for preparing a tert-alkyl carboxylic acid ester having a tert-alkyl moiety which is useful as its protective group. The tert-alkyl carboxylic acid ester is useful for pharmaceuticals such as antibiotics, raw materials for chemicals, intermediates, and the like.

2. Discussion of the Related Art

As processes for preparing a tert-alkyl carboxylic acid ester, there have been known 1) a process comprising reacting an acid chloride of a carboxylic acid with a tertiary alcohol in the presence of dimethylaniline [*Organic Synthesis III*, 142], 2) a process comprising treating malonic acid with isobutylene as a vinylidene compound in the presence of sulfuric acid [*Organic Synthesis IV*, 261], and the like.

However, in the process 1), there are some defects such that the preparation process is long, and the procedures are complicated since this process necessitates a process for preparing an acid chloride of a carboxylic acid, and that this process is economically disadvantageous since this process necessitates an expensive base such as dimethylaniline. Also, in the process 2), there are some defects that the reaction product is easily hydrolyzed by sulfuric acid used in the reaction, and the vinylidene compound is likely to be polymerized under the given reaction conditions.

An object of the present invention is to provide a process for simply, conveniently and industrially advantageously preparing a tert-alkyl carboxylic acid ester in a high yield.

The above and other objects of the present invention will be apparent from the following description.

SUMMARY OF THE INVENTION

According to the present invention, there is provided a process for preparing a tert-alkyl carboxylic acid ester represented by the formula (III):

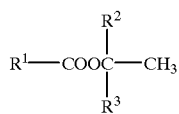

(III)

wherein $R^1$ is an organic group; and each of $R^2$ and $R^3$ is independently an alkyl group having 1 to 4 carbon atoms, comprising reacting a carboxylic acid represented by the formula (I):

$$R^1\text{---COOH} \tag{I}$$

wherein $R^1$ is as defined above, with a vinylidene compound represented by the formula (II):

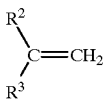

(II)

wherein $R^2$ and $R^3$ are as defined above,
in the presence of a phosphorus halide.

DETAILED DESCRIPTION OF THE INVENTION

According to the present invention, as described above, there can be obtained a tert-alkyl carboxylic acid ester represented by the formula (III):

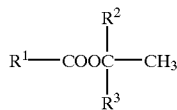

(III)

wherein $R^1$ is an organic group; and each of $R^2$ and $R^3$ is independently an alkyl group having 1 to 4 carbon atoms, by reacting a carboxylic acid represented by the formula (I):

$$R^1\text{---COOH} \tag{I}$$

wherein $R^1$ is as defined above,
with a vinylidene compound represented by the formula (II):

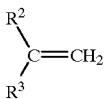

(II)

wherein $R^2$ and $R^3$ are as defined above,
in the presence of a phosphorus halide.

The carboxylic acid represented by the formula (I) is not limited to specified ones, as long as the object of the present invention is not hindered. In the formula (I), $R^1$ includes, for instance, alkyl groups, aralkyl groups, aryl groups and heterocyclic groups, each of which may have a substituent.

Representative examples of the alkyl group include substituted or unsubstituted, linear or branched alkyl groups having 1 to 20 carbon atoms, preferably 1 to 8 carbon atoms. Concrete examples of the alkyl groups include, for instance, methyl group, ethyl group, propyl group, isopropyl group, n-butyl group, isobutyl group, pentyl group, heptyl group, and the like.

Representative examples of the aralkyl group include substituted or unsubstituted, linear or branched aralkyl groups having 7 to 20 carbon atoms, preferably 7 to 10 carbon atoms. Concrete examples of the aralkyl groups include, for instance, benzyl group, phenylethyl group, phenylpropyl group, and the like.

Representative examples of the aryl group include substituted or unsubstituted aryl groups having 1 to 5 aromatic rings. Concrete examples of the aryl groups include, for instance, aryl groups having 6 to 20 carbon atoms such as phenyl group, naphthyl group and phenanthryl group.

Representative examples of the heterocyclic group includes substituted or unsubstituted heterocyclic groups having 1 to 3 atoms selected from the group consisting of oxygen atom, nitrogen atom and sulfur atom. Concrete examples of the heterocyclic groups include, for instance, furyl group, pyrrolyl group, imidazolyl group, pyridyl group, pyrimidinyl group, oxazolyl group, thienyl group, thiazolyl group, benzofuryl group, quinolyl group, 8-oxo-5-thia-1-azabicyclo[4,2,0]oct-2-ene-2-yl group, and the like.

The substituent which may exist in $R^1$ is not limited to specified ones as long as the object of the present invention is not hindered. Examples of the substituents include substituted or unsubstituted, linear or branched alkyl groups having 1 to 20 carbon atoms, such as methyl group, ethyl group, propyl group, butyl group and pentyl group; substituted or unsubstituted aryl groups having 6 to 20 carbon atoms, such as phenyl group and naphthyl group; substituted or unsubstituted, linear or branched aralkyl groups having 7 to 20 carbon atoms, such as benzyl group and phenylethyl group; substituted or unsubstituted heterocyclic groups having 1 to 3 atoms selected from the group consisting of oxygen atom, nitrogen atom and sulfur atom, such as furyl group, pyrrolyl group, imidazolyl group, pyridyl group, pyrimidinyl group, oxazolyl group, thienyl group, thiadiazolyl group and benzofuryl group; substituted or unsubstituted, linear or branched alkoxy groups having 1 to 10 carbon atoms, such as methoxy group, ethoxy group and propoxy group; halogen atoms, such as fluorine atom, chlorine atom, bromine atom and iodine atom; alkyl esters which may have a substituent such as a substituted or unsubstituted alkyl ester group such as methoxycarbonyl group, ethoxycarbonyl group or propoxycarbonyl group, an aryl ester group such as phenoxycarbonyl group, or a substituted or unsubstituted aralkyl ester group such as benzyloxycarbonyl group or nitrobenzyloxycarbonyl group; substituted or unsubstituted alkyl ketones, such as acetyl group and propionyl group; substituted or unsubstituted aryl ketones, such as benzoyl group; amide groups such as carbamoyl group, acetoamino group and benzamide group; ureido groups such as carbamoylamino group and phenylaminocarbamoyl group, and the like.

In the vinylidene compound represented by the formula (II), each of $R^2$ and $R^3$ is independently an alkyl group having 1 to 4 carbon atoms. Concrete examples of the alkyl groups include methyl group, ethyl group, propyl group, isopropyl group, n-butyl group, and the like. Representative examples of the vinylidene compound include isobutylene, 2-methyl-1-butene, 2-methyl-1-pentene, and the like. Among them, isobutylene can be preferably used.

The amount of the vinylidene compound represented by the formula (II) is not limited to specified ones. It is desired that the amount of the vinylidene compound is usually not less than 1.5 moles, preferably not less than 1.8 moles, per one mole of the carboxylic acid represented by the formula (I), from the viewpoint of reactivity, and not more than 10 moles, preferably not more than 3 moles, per one mole of the carboxylic acid represented by the formula (I), from the viewpoint of economics.

In the present invention, one of great features resides in that the carboxylic acid is reacted with the vinylidene compound in the presence of a phosphorus halide. Since the phosphorus halide is employed in the reaction, the tert-alkyl carboxylic acid ester can be simply, conveniently and industrially advantageously prepared in a high yield.

The phosphorus halide includes, for instance, phosphorus halides such as phosphorus oxytrichloride, phosphorus trichloride, phosphorus pentachloride and dichlorophosphonic acid. Among those phosphorus halides, phosphorus oxytrichloride, phosphorus trichloride and dichlorophosphonic acid are preferable, from the viewpoint of reactivity.

It is desired that the amount of the phosphorus halide is not less than 0.05 moles, preferably not less than 0.15 moles, per one mole of the carboxylic acid, from the viewpoint of reactivity, and not more than 1 mole, preferably not more than 0.4 moles, per one mole of the carboxylic acid, from the viewpoint of economics.

During the reaction of the carboxylic acid with the phosphorus halide, a solvent can be used. The solvent is not limited to specified ones, as long as the reaction is not hindered. The solvent includes, for instance, hydrocarbon solvents such as heptane and cyclohexane; aromatic solvents such as benzene, toluene and xylene; halogenated solvents such as dichloroethane and chlorobenzene; ester solvents such as ethyl acetate and butyl acetate; ether solvents such as tetrahydrofuran and dioxane, and the like. Among those solvents, aromatic solvents, especially toluene, are preferable from the viewpoint of economics. It is desired that the amount of the solvent is usually 10 to 2000 parts by weight, preferably 50 to 200 parts by weight, based on 100 parts by weight of the carboxylic acid.

In addition, during the reaction of the carboxylic acid with the phosphorus halide, it is preferable to use a catalytic amount of water, from the viewpoint of accelerating the reaction. It is desired that the amount of water is usually 0.05 to 0.15 moles, preferably 0.07 to 0.12 moles, per one mole of the carboxylic acid, from the viewpoint of rapidly carrying out the reaction.

The reaction temperature during the reaction of the carboxylic acid with the phosphorus halide cannot be absolutely determined. It is desired that the temperature is usually 0° to 40° C. or so, preferably 10° to 30° C. or so, from the viewpoints of reaction rate and inhibition of ester decomposition.

The reaction time cannot be absolutely determined because the reaction time varies depending upon reaction temperature and the like. The reaction time can be until the termination of the reaction, and is usually 1 to 24 hours or so. Incidentally, the termination of reaction can be confirmed by using gas chromatography (GC), high-performance liquid chromatography (HPLC), and the like.

The reaction product thus prepared is a tert-alkyl carboxylic acid ester represented by the formula (III).

After the termination of the reaction, for instance, the reaction mixture is added dropwise to water or an aqueous alkali with stirring, or alternatively water or an aqueous alkali is added dropwise to the reaction mixture with stirring, and the mixture is allowed to separate into two layers. The organic layer can be used after the organic layer is washed with water or an aqueous alkali and dried over a desiccant such as magnesium sulfate, or after the organic solvent is distilled off to precipitate crystals.

The tert-alkyl carboxylic acid ester prepared according to the present invention can be suitably used, for instance, as intermediates for pharmaceuticals such as antibiotics. In addition, the process of the present invention can be also utilized for a process for protecting carboxyl group in the carboxylic acid.

EXAMPLES

The present invention will be described in further detail on the basis of the following working examples, without intending to limit the scope or spirit of the present invention thereto.

Example 1

A 200-ml four-neck flask was charged with a solution prepared by dissolving 13.9 g of bromoacetic acid and 11.3 g of isobutylene in 32 ml of toluene, and 0.18 g of water. To the flask was added dropwise 3.1 g of phosphorus oxytrichloride at 10° C., and the mixture was stirred at 25° C.

Next, with monitoring the reaction by gas chromatography, the reaction mixture was added dropwise to 65 ml of a saturated aqueous sodium bicarbonate after 6 hours passed from the initiation of the reaction.

Next, the organic layer was collected, washed with brine, and dried over anhydrous magnesium sulfate. Thereafter, the solvent was distilled off under reduced pressure, to give 19 g of an oily residue (crude yield: 95%). The resulting residue was examined by NMR and IR. The results are as follows. It was confirmed from the following results that the resulting compound was tert-butyl bromoacetate.

(1) IR (neat) ) ν (cm$^{-1}$): 1740

(2) $^1$H-NMR (CDCl$_3$) δ (ppm): 1.49 (s, 9H), 3.75 (s, 2H)

Example 2

A one-liter four-neck flask was charged with 85 g (1.0 mole) of cyanoacetic acid, 200 ml of toluene, 112 g (2 moles) of isobutylene and 1.8 ml of water. To the flask was added dropwise 30.6 g of phosphorus oxytrichloride at 10° C., and the mixture was stirred at 20° C.

Next, with monitoring the reaction by gas chromatography, the reaction mixture was washed with 1 N aqueous sodium hydroxide after 9 hours passed from initiation of the reaction.

Next, the organic layer was collected, washed with brine, and dried over anhydrous magnesium sulfate. Thereafter, the solvent was distilled off under reduced pressure, to give 130 g of a residue (crude yield: 92%). The resulting residue was examined by IR. The results are as follows. It was confirmed from the following results that the resulting compound was tert-butyl cyanoacetate.

(1) Boiling point: 90° C. [1600 Pa (12 mmHg)]

(2) IR (neat) ν (cm$^{-1}$): 2250, 1730

According to the process of the present invention, the tert-alkyl carboxylic acid ester can be simply and conveniently and industrially advantageously prepared in a high yield.

What is claimed is:

1. A process for preparing a tert-alkyl carboxylic acid ester represented by the formula (III):

(III)

wherein R$^1$ is an organic group; and each of R$^2$ and R$^3$ is independently an alkyl group having 1 to 4 carbon atoms, comprising reacting a carboxylic acid represented by the formula (I):

(I)

wherein R$^1$ is as defined above, with a vinylidene compound represented by the formula (II):

(II)

wherein R$^2$ and R$^3$ are as defined above, in the presence of a phosphorus halide.

2. The process according to claim 1, wherein the phosphorus halide is phosphorus oxytrichloride, phosphorus trichloride or dichlorophosphonic acid.

3. The process according to claim 1, wherein the vinylidene compound is isobutylene.

4. The process according to claim 1, wherein the carboxylic acid is reacted with the vinylidene compound in the presence of the phosphorus halide and a catalytic amount of water.

* * * * *